United States Patent [19]

Kulkarni et al.

[11] 4,263,274

[45] Apr. 21, 1981

[54] ANTIPERSPIRANT COMPOSITIONS AND METHODS

[75] Inventors: Arun B. Kulkarni; Kakubhai R. Vora, both of East Brunswick, N.J.

[73] Assignee: Johnson & Johnson, New Brunswick, N.J.

[21] Appl. No.: 706,082

[22] Filed: Jul. 16, 1976

[51] Int. Cl.$^3$ .............................................. A61K 9/14
[52] U.S. Cl. ...................................... 424/46; 424/47; 424/65; 424/362; 424/363
[58] Field of Search .................... 424/363, 46, 362, 47, 424/65

[56] References Cited

U.S. PATENT DOCUMENTS

| 3,251,824 | 5/1966 | Battista | 424/362 X |
| 3,868,955 | 3/1975 | Steiger et al. | 128/296 |

FOREIGN PATENT DOCUMENTS 2453139  5/1975  Fed. Rep. of Germany ............. 424/65

Primary Examiner—Dale R. Ore

[57] ABSTRACT

Compositions and methods for reducing perspiration with aldehyde polysaccharide compounds. Suitable aldehyde polysaccharide compounds include dialdehyde cellulose, dialdehyde starch, and the like.

8 Claims, No Drawings

ANTIPERSPIRANT COMPOSITIONS AND METHODS

SUBJECT OF THE INVENTION

This invention is concerned with compositions and methods for inhibiting perspiration; and more particularly it is concerned with compositions and methods for reducing perspiration with aldehyde polysaccharide compounds.

BACKGROUND OF THE INVENTION

Antiperspirants are generally considered to be essential items of personal hygiene. Reduction in volume of perspiration is desirable to avoid the discomforts associated with perspiration which is not immediately evaporated. In addition to the general and frequently extreme discomfort of excessive perspiration, there may also be problems of undesirable oder and deleterious effect on clothing. Moreover sufficient instances of clinical hyperhydrosis exist for which efficient therapy is sought. Currently there are available antiperspirant products which are effective in reducing perspiration volume by about 25 to 35 percent. These are primarily aluminum salts. However, there has been increasing concern about long-term inhalation hazards of metal salts in general, and the reported ability of aluminum salts to produce lung tumors in animals after prolonged inhalation (Drew et al., "Inhalation Studies With a Glycol Complex of Aluminum-Chloride-Hydroxide," Arch. Environ. Health., 28, 321–326 (1974)) has rendered it desirable to seek non-metallic materials having anhidrotic activity. Moreover, many salts cause weakening of fabric or subsequent deterioration on ironing. Additionally, they may cause discoloration of fabric by acid-sensitive dyes and some may remain on the fabric and discolor the fabric on reaction with detergent.

Although non-metallic compounds have been reported from time to time to have anhidrotic properties, none have appeared to replace the presently available metallic compounds. Thus, for example, formaldehyde and glutaraldehyde have been reported by Gordon et al (J. Invest. Derm. 53(6), 436–439 (1969)) to have anhidrotic properties but are not useful because of strong odor, highly irritating effect on the skin and/or high skin permeability or skin staining. Other aldehydes are not generally known to have similar anhidrotic properties. Gordon et al found that eleven other aldehydes which included glyoxal, a dialdehyde, showed no anhidrotic properties.

It is an object of the present invention to provide compositions and methods for inhibiting perspiration without the inhalation hazards of metal salts. It is particularly an object to provide for such compositions and methods without the use of salts of aluminum. It is further an object of the present invention to provide compositions and methods for inhibiting perspiration by the use of non-metallic compositions which may be applied directly to the skin without having undesirable side effects such as irritation or darkening of the skin. It is still further an object of the present invention to provide for such non-metallic compositions which are without harmful effect on fabrics. These and other objects will become evident from the following specification and claims.

BRIEF STATEMENT OF THE INVENTION

According to the present invention it has been discovered that by employing a composition comprising an aldehyde polysaccharide compound, effective perspiration control may be achieved without use of metallic anhidrotic agents. It has further been found that it may be accomplished to an extent comparable to or better than can be accomplished by methods and compositions employing metal containing antiperspirants and without the undesirable side effects of compounds such as formaldehyde and glutaraldehyde.

Although certain dialdehyde starches or dialdehyde celluloses have been reported to act on biological systems or products, they had been employed for different problems and oftentimes with dialdehyde polysaccharides of a different nature. Thus, a water-soluble dialdehyde starch is taught in U.S. Pat. No. 3,679,792 to be incorporated in chewing gum compositions as a cariostatic agent. Dialdehyde starch is taught in U.S. Pat. No. 3,093,439 to be useful as a tanning agent. Aldehyde polysaccharides are taught to be incorporated into absorbent pads for odor control in U.S. Pat. No. 3,868,955. It is not known to apply aldehyde polysaccharides to the epidermis of living subjects for modifying or interacting with the skin or for affecting a physiological function in which the skin is a participant.

DETAILED DESCRIPTION OF THE INVENTION

It has now been discovered that aldehyde polysaccharide compounds as hereinafter defined are effective in inhibiting perspiration, i.e., reducing the volume of perspiration produced. Moreover compositions of aldehyde polysaccharides are not subject to the problems of high skin irritation associated with formaldehyde and glutaraldehyde or to the problems of inhalation hazards associated with metal salts. Additionally, aldehyde polysaccharides do not cause deterioration of fabrics, or staining of fabrics or skin.

By the expression "aldehyde polysaccharide compound" as herein employed is meant high molecular weight polysaccharides, such as for example, starch and cellulose and the like which have been modified by controlled oxidation of certain of the hydroxyl groups in a monosaccharide unit to aldehyde groups. Typically, the aldehyde polysaccharides are those in which the aldehyde groups are formed by the oxidation of the vicinal hydroxyl groups of a monomer unit of a polysaccharide polymer in the following manner

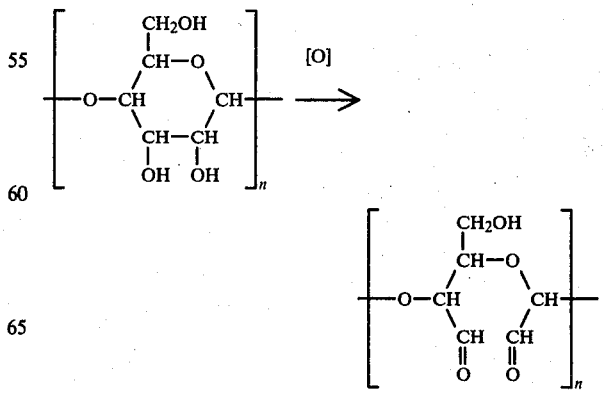

wherein in the above equation n represents an integer.

When, as above, the aldehyde groups are formed by vicinal oxidation, two aldehyde groups are formed simultaneously from each monomer unit, the products are frequently referred to as "dialdehyde" polysaccharides. Depending on the nature and source of the polysaccharide, the polysaccharide portion may be specified according to their nature, e.g., as starch or cellulose. Thus, the aldehyde polysaccharide may be specified as dialdehyde cellulose or dialdehyde starch. Dialdehyde celluloses are particularly preferred.

Suitable aldehyde polysaccharides are generally prepared by periodate oxidation of starch or cellulose carried out by contacting an aqueous solution of periodic acid or sodium periodate and acid with the appropriate polysaccharide at temperatures of from about 20°–40° C. at pH below about 2 for time sufficient to complete the reaction. The amount of oxidizing reagent employed varies with the extent of oxidation sought to be accomplished. Other oxidizing agents such as lead tetraacetate in glacial acetic acid may be employed, although less preferred. Still other oxidizing agents such as hydrogen peroxide and ozone may be employed to obtain oxidized polysaccharides but since the oxidation is less selective and the products are less well defined, products so obtained are less desirable. The preparation of dialdehyde polysaccharides suitable for use in present invention can be found in standard texts, journal articles as well as in the patent art. Thus, for example, the procedure for the oxidation of vicinal hydroxyl of starch and cellulose may be found in an article by Jackson and Hudson, J. Am. Chem. Soc. 59, 2049 (1937). Preparative methods for dialdehyde starch may also be found in U.S. Pat. Nos. 2,648,629 of W. Dvonch et al, 2,713,533 and 3,269,964 of J. H. Curtis; methods for dialdehyde cellulose may be found in U.S. Pat. No. 3,086,969 of J. E. Slager.

The aldehyde polysaccharides suitable for the compositions and methods of the present invention need not be and generally are not those in which the vicinal hydroxyl groups in all the monomer units have been converted to the aldehyde groups. Suitable aldehyde polysaccharides for the practice of the present invention may be characterized by the degree or extent of oxidation and/or by the weight percent aldehyde group. Those in which at least about 10 percent and up to 100 percent of the vicinal hydroxyls have been oxidized are contemplated. By "percent oxidized" as above employed or by "degree of oxidation" as hereinafter employed is meant the extent of conversion of hydroxyl groups to aldehyde groups in the polysaccharide and not to the level of oxidation achieved by a particular group, i.e., acid or carbon dioxide. Moreover, it is recognized that pendant primary hydroxyl groups may also be oxidized to aldehyde groups; however, in view of the preferred methods of preparation of the aldehyde polysaccharides, most of the aldehyde groups are expected to arise from the oxidation of the vicinal hydroxyl groups and the percent oxidation as herein employed is intended to refer primarily to aldehyde groups arising in this way. Preferably, the aldehyde polysaccharides are at least 70 percent oxidized. Although from the standpoint of efficacy the polysaccharides may be 100 percent oxidized, the use of such completely oxidized polysaccharides is limited by the problems encountered in their synthesis and isolation. Generally, the upper oxidation level of available aldehyde polysaccharides are those which have undergone about 95 percent conversion to the oxidized (aldehyde) state but aldehyde polysaccharides as herein employed are not to be limited thereto.

The extent of oxidation may be determined by the borohydride method for determination of aldehyde and ketone groups as hereinafter described. The analytical method utilizes the selective reduction of carbonyl compounds by borohydrides, particularly sodium borohydride and may be carried out as described in an article by Rankin, J. C. et al, "Determination of Dialdehyde Units in Periodate - Oxidized Cornstarches", Anal. Chem 28, 1012 (1956) or a modification thereof. Briefly, sodium borohydride is added dropwise to a solution of aldehyde polysaccharide in aqueous sodium acetate, buffered with boric acid-borax solution and the hydrogen evolved measured. It is to be noted, however, that frequently designation of extent of oxidation in technical literature, as well as in specifications accompanying commercially available aldehyde polysaccharides, may be a designation of percent oxidizing agent consumed rather than percent oxidation to the aldehyde polysaccharide compound.

The aldehyde polysaccharide compounds may also be described in terms of weight percent aldehyde groups. Since generally two aldehyde groups are formed per monomer unit on the oxidation of vicinal hydroxyl groups, the percent aldehyde group may be calculated as the aldehyde group per equivalent weight of aldehyde polysaccharide unit. Thus, the percent aldehyde group is based on the assumption of aldehyde formation solely by vicinal oxidation although it is recognized that certain of the pendant hydroxyl groups may undergo oxidation.

The aldehyde polysaccharide compounds are further defined by molecular size which may be expressed as degree of polymerization and/or molecular weight. The aldehyde polysaccharides suitable for the practice of the present invention generally have a degree of polymerization of at least 250 repeating units per molecule. No method is currently available in which the degree of polymerization of dialdehyde polysaccharide may be directly measured by solution viscosity measurements since the standard TAPPI (Technical Association of Paper and Pulp Industries) method of determining degree of polymerization by measuring solution viscosity of polysaccharide in cupriethylenediamine (T230-su-66 available from TAPPI) solution causes rapid degradation of the aldehyde polysaccharide. However, by employing the TAPPI method and making determinations on untreated polysaccharides and thereafter on "blank processed polysaccharides" it has been possible to estimate the degree of depolymerization undergone during the processing of polysaccharides. By "blank processed" is meant subjecting the polysaccharides to oxidizing process conditions except for the presence of the oxidizing agent. Under such conditions it has been found that the polysaccharides may undergo a degree of depolymerization to an extent of up to about 50 percent. It is expected that a similar degree of depolymerization occurs in the preparation of dialdehyde cellulose. Thus, the dialdehyde polysaccharide useful in the practice of the present invention may be of a degree of polymerization significantly lower than that of the starting polysaccharides. It has been found that aldehyde polysaccharide compounds suitable for the practice of the present invention may be obtained by proper selection of the polysaccharide starting materials. Generally the polysaccharides suitable as starting materials in the preparation of the aldehyde polysaccharide may be characterized as being water insoluble polymers having a degree of polymerization of from about 400 to about 2000 or more or a molecular weight in the range of from about 60,000 to about 325,000. When the aldehyde polysaccharide is a dialdehyde cellulose, the starting cellulose may be one having a molecular weight anywhere in the broad range. When the aldehyde polysaccharide is dialdehyde starch, the starting starch is preferably in the molecular weight range of from about 129,000 to about 200,000. The aldehyde polysaccharides obtainable from these celluloses and starches may have a degree of polymerization of from about 200 to 1000, preferably 400 or greater. The molecular weight range may be of from about 32,000 to about 162,000.

The aldehyde polysaccharide compounds of the degree of oxidation above-described and of the degree of polymerization above-described, are generally white solids, difficultly soluble i.e., substantially insoluble in water but tend to swell in water and aqueous media. They are substantially insoluble in non-polar organic solvents. The aldehyde polysaccharide compounds are adapted to be incorporated in a carrier suitable for application as hereinafter described. Some of the suitable dialdehyde polysaccharides are available commercially under various trade names, such as Sumcel and Sumstar-190(dialdehyde celluloses obtained by the oxidation of wood cellulose and dialdehyde starches obtained by the oxidation of corn starch, respectively, products of Miles Laboratories, Elkhart, Indiana).

The methods of the present invention may be carried out by applying to the epidermal surfaces where inhibition of perspiration is desired, a perspiration inhibiting amount (i.e., a perspiration volume reducing amount) of an aldehyde polysaccharide compound. Although the exact amount is not critical, generally an amount sufficient to supply from about 0.02 to about 1 mg. per square cm. of epidermal surface area is employed. The preferred amount depends on the extent of perspiration necessary to be controlled, on the place and method of application, and on the particular composition employed. Thus, it is expected that larger amounts may be necessary for the more active sites such as the axillary area. For ordinary perspiration control, from about 0.02 to about 0.4 mg./square cm. is applied. For clinical control of hyperhydrosis, higher amounts are preferably employed.

Although the exact mechanism by which the aldehyde polysaccharides exert antiperspirant activity has not been established, it has been found that the presence of a certain amount of aldehyde group is essential. This amount of aldehyde may be supplied by employing a relatively larger amount of a less oxidized aldehyde polysaccharide compound or a smaller amount of a more highly oxidized aldehyde polysaccharide compound. Further, it has been found that other factors such as the $\alpha$ or $\beta$ linkage may be important within the aldehyde polysaccharide compounds. Thus, dialdehyde celluloses are preferred and may be employed in lesser amounts.

The effective amount of aldehyde polysaccharide compound may be administered in compositions containing at least about 0.2 percent by weight of aldehyde group which when applied in an amount sufficient to cover the desired skin surfaces provides sufficient useful antiperspirant activity. Although lesser amounts may be shown to have some antiperspirant activity, it is usually not considered sufficient from a practical standpoint. The desired amount of aldehyde group may be supplied in compositions in which the aldehyde polysaccharide compound is present in an amount of at least 0.5 percent by weight of ultimate composition, but generally about 1 percent by weight or higher. In view of the diluting and possible partial deactivating effect of the carrier and loss on application, the treating compositions preferably contain at least about 4 percent by weight. (This amount of aldehyde polysaccharide compound is expected to supply at least about 1 percent aldehyde groups by weight when the degree of oxidation is about 70 percent.) Of course, larger amounts are more effective, although compositions containing more than about 35 percent would not be considered practical in treating compositions since then most of the aldehyde polysaccharide compound would remain unutilized. When the aldehyde polysaccharide is dialydehyde cellulose lesser amounts may be employed. In concentrate compositions the aldehyde polysaccharides may be present in larger amounts and may even constitute a major portion of the composition. The preferred range may vary with the carrier; the preferred ranges and carriers for the various methods of application are subsequently described.

The application to the epidermal surface is made topically, preferably in a suitable carrier. The carrier is generally a cosmetic or pharmaceutical carrier intended for topical use although it may be merely an aqueous suspension. The aldehyde polysaccharide compound may be supplied in a solid, liquid, spray or semi-solid form and include lotions, ointments, aerosols, liquid sprays, solutions, creams, pulverized mixtures, gel sticks, liquid roll-ons and the like. Employing the appropriate compositions, topical application may be made by dusting, spraying, rubbing, etc. Representative suitable compositions and their preparation are hereinafter described.

Although the exact nature of the carrier or the form in which it is applied, i.e., as dry solid, liquid, etc. is not critical, it is critical that the aldehyde polysaccharide be substantially uniformly dispersed in the carrier in view of its insoluble nature. Depending on the nature of the carrier, an appropriate composition may be prepared merely be thorough mixing. In certain compositions, e.g., liquid compositions, it may be desirable to include a dispersing agent to insure good dispersion, although it is essential only that good dispersion be achieved just prior to application such as by shaking.

In the preparation of the compositions, particularly to achieve the homogeneity desired, the particle size of the aldehyde polysaccharide compound should be of a particle size which will pass through a 200 mesh sieve (U.S. Standard). Preferably, powder of a smaller particle size is employed, although for dusting compositions, powders meeting the above specification are entirely suitable. Preferred particle sizes of the aldehyde polysaccharides to be employed are those passing through a 325 mesh screen.

One method of application is dry spraying onto the epidermal surfaces by use of a powder aerosol composition. A composition suitable for use in such method comprises an aldehyde polysaccharide compound powder in admixture (a) with a lubricant and a propellant which facilitate the dispensing of the antiperspirant and (b) preferably with a surfactant which facilitates the wetting and spreading properties of the dispensed aldehyde polysaccharide powder on the epidermal surfaces to render efficient the functioning of the antiperspirant.

The lubricant dispensing aid which reduces clogging and which also contributes to reducing the fogging and clouding effect is a liquid carrier which is preferably a synthetic fluid silicone polymer (organopolysiloxane) but may be one of a number of volatile or non-volatile, substantially anhydrous and non-water-gathering or non-hygroscopic materials such as organic esters of higher fatty acids such as isopropyl myristate, isopropyl palmitate or isopropyl stearate; fatty acids; fatty alcohols; mineral oils; vegetable oils; or hydrocarbon oils such as undecane, dodecane, or isoparaffins. The preferred organopolysiloxane carrier and emollient may be of any of dialkyl, or phenyl and alkyl, or alkyl or substituted polysiloxane, cyclic or linear, which may be represented by the formula:

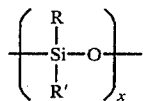

where R and R' are independently lower alkyl, phenyl or vinyl, and x is an integer. The suitable organopolysiloxanes include water-insoluble fluid compounds with a viscosity in the range of from about 40 to about 400 centistokes, preferably in the range of from about 100 centistokes to about 350 centistokes. One suitable polydimethylsiloxane is Dow Corning Q2-1053 or Dow Corning 344 Fluid (products of Dow Corning Corporation). Other suitable organosiloxane fluids which may be employed include dimethylcyclic compounds such as Dow Corning F-128 Fluid and Dow Corning Q1-3597 Fluid, dimethyl linear compounds such as Dow Corning 225 Fluid and Dow Corning 200 Fluid, a phenylmethyl linear compound such as Dow Corning 556 Fluid and polymer containing branched chain polysiloxane such as Dow Corning Silicone Polymer MDX4-4140. Still other examples of suitable silicone fluids are the SF-96 series of dimethylpolysiloxanes, products of the General Electric Company; organosilicone polymers L-531 and L-530 and dimethylsilicone fluid L-45, products of Union Carbide. Volatile silicone 7207 and 7158, products of Union Carbide Corp., are also useful.

The non-reactant propellants are preferably fluorohydrocarbon blends although numerous fluorohydrocarbons and paraffinic hydrocarbons may be employed singly or as mixtures of fluorohydrocarbons and paraffinic hydrocarbons. Propellants that can be used alone include dichlorodifluoromethane (Propellant 12), monochlorodifluoroethane (Propellant 142b), and isobutane. Suitable propellant mixtures include: chloropentafluoroethane (Propellant 115) and dichlorotetrafluoroethane (Propellant 114) with ratios varying from about 10/90 to 70/30; propane and isobutane with ratios varying from about 10/90 to 50/50; dichlorodifluoromethane and n-butane with ratios varying from about 10/90 to 90/10; dichlorodifluoromethane and isobutane with ratios varying from about 10/90 to 90/10; and fluorohydrocarbon mixtures such as dichlorodifluoromethane with trichlorotriflouroethane or dichlorotetrafluoroethane or dichlorotetrafluoroethane or trichloromonofluoromethane (Propellant 11) with ratios varying from about 99/1 to 40/60. The preferred propellant mixture for use in the present invention is dichlorodifluoromethane and dichlorotetrafluoroethane (Propellant 12/Propellant 114) in about a 40/60 ratio. The fluorinated hydrocarbons suitable as propellants are available commercially under trade names such as Freons, Ucons, Genetrons, etc. The appropriate propellant may be identified by the trade name followed by a number corresponding to the foregoing propellant number.

In addition to the foregoing essential ingredients of the aerosol composition, the composition may and preferably does contain a surfactant. The surfactant may improve the performance characteristics of the antiperspirant after it has been deposited on the skin surface. Suitable surface active agents are those of the water-soluble non-ionic type derived from reaction between long chain alcohols and ethylene oxide or glycol ether or propylene oxide; or between long chain fatty acids and ethylene oxide or propylene oxide; or sugar alcohols and inner anhydrides or ethers thereof. Particularly effective materials are the water-soluble organic non-ionic polyalkylene oxide surface-active agents. Such materials generally are the water-soluble condensates of polyalkylene oxide containing from about 5 to 60 alkylene oxide groups with a hydrophobic organic group, the latter group containing at least about 5 and usually about 8 to 30 carbon atoms. It is preferred to use a polyalkylene oxide ether of higher aliphatic alcohols. Suitable fatty alcohols having a hydrophobic character, and preferably 8 to 22 carbons, are lauryl, tridecyl, myristyl, cetyl, stearyl and oleyl alcohols which may be condensed with an appropriate amount of ethylene oxide, preferably about 6 to 30 moles per mole of alcohol. A typical product is tridecyl alcohol (1 mole) condensed with about 10 moles of ethylene oxide.

Further suitable non-ionic materials are the polyalkylene oxide condensates of alkyl phenol such as the polygolycol ethers of alkyl phenol wherein the alkyl group has about 6 to 60 carbons and about 5 to 30 moles of ethylene oxide, specific examples of which are Igepal CO-630 and 710. Others include sorbitan monofatty acid esters and their polyoxyethylene derivatives, such as sorbitan mono-oleate, mono-laureate or mono-stearate and their polyoxyethylene derivatives; and mono- and di-ethanolamides or long chain fatty acids such as coco acid poly-diethanolamide, stearic acid mono-ethanolamide, myristic acid mono-ethanolamide, etc. Particularly useful are condensation products sold under trade names such as the Tweens (products of ICI America, Inc., Atlas Chemicals Division, Wilmington, Del.).

In general, the antiperspirant aerosol composition is formulated to contain the aldehyde polysaccharide antiperspirant in a normal range of from about 2 to 15 percent by weight of the total composition, generally with a preferred range extending from about 5 to 10 percent by weight. The non-hygroscopic lubricant is generally employed in amounts ranging from about 0.5 to 10 percent by weight with a range of about 4.5 to 8 percent by weight preferred. The propellant liquid constitutes essentially the remainder of the composition and is generally employed in amounts of from about 75 to 95 percent by weight of the aerosol composition. When employed, surfactant may be added in amount up to about 1 percent of the total composition. Also, if desired fragrance and other ingredients may be added, not to exceed about two percent of the total composition. Preferably, the amount added is from about 0.1 to about 0.5 percent.

In preparing the antiperspirant compositions, the finely divided aldehyde polysaccharide compound is placed in the ultimate spray container. Fragrance, if employed, is admixed with the organopolysiloxane or other lubricant and the resulting mixture filtered through a fiber filter Thereafter the organopolysiloxane mixture is charged into the container. Following this, the container is filled with the desired amount of propellant or propellant mixture. The aerosol product is suitable for application onto epidermal surfaces.

Another method of application is dusting onto the epidermal surfaces by using a dusting composition. This method is particularly suitable for covering large areas or for administering higher amounts of antiperspirant compound such as may be desired for treating clinical hyperhidrosis. Suitable dusting compositions comprise an aldehyde polysaccharide compound in admixture with a cosmetically acceptable inert powder carrier with certain carriers, lubricants and flow additives preferably included. Also, if desired, fragrance and minor amounts of other optional ingredients including coloring agents and preservatives such as sorbic acid, methyl and propyl parabens and the like may be added. Suitable carriers include corn starch, talc, and like powders. Such powders may be employed singly, as mixtures or may be modified with other inert powders. Other powders include zinc oxide and dicalcium phosphate. Also powders such as kaolin may be included in minor amounts. Suitable lubricants include calcium and magnesium salts of fatty acids; suitable flow additives include tricalcium phosphate and the like. Particularly suitable blends of lubricants and flow additives are tricalcium phosphate with magnesium stearate, calcium stearate, zinc stearate, hydrogenated vegetable oils and the like.

Powder compositions permit inclusion of higher amounts of the aldehyde polysaccharide compound. Thus, amounts of from 1 percent to about 25 percent or more by weight of the active ingredient may be formulated in the composition. The total amount of lubricant and/or flow additive generally is in the range of from about 0.2 percent to about 2 percent by weight, whether employed singly or in a blend. Fragrance and other optional ingredients, if employed, are added in an amount not to exceed about 1 percent.

Dry powder compositions may be prepared by first sieving the lubricant and carrier components, preferably through a 325 mesh sieve, and thereafter mixing thoroughly in a blender. To the dry blended mixture is then added the aldehyde polysaccharide, previously sieved through a 325 mesh sieve, and the resulting mixture thoroughly blended followed by the optional addition of fragrance and blending. The resulting dry powder mixture is suitable for use in perspiration control.

Still another method of application is by rubbing, spraying, or otherwise administering a liquid composition onto the epidermal surfaces. In the liquid compositions the aldehyde polysaccharide compound is in admixture with a liquid carrier, generally with a dispersing agent and may include other ingredients such as wetting agents, co-vehicles, thickening agents and the like. The nature of the non-active ingredients may vary depending on whether the liquid composition is to be administered by rubbing, by spraying, by employing a roll-on dispenser, etc. In addition, fragrance and other optional ingredients may be employed in minor amounts.

In liquid compositions suitable for application without special dispensers, the compositions may be prepared in water with or without a dispersing agent such as a gum tragacanth solution, and with or without other additaments such as preservatives or fragrance. Preferred liquid compositions for use without special dispensers comprise an aldehyde polysaccharide compound dispersed in a nonaqueous liquid vehicle and may include a wetting agent and preferably includes a thickening agent. Suitable liquid carriers or vehicles include ethanol, isopropanol, or lower alkanols and blends of alkanols, and witch hazel. Liquid covehicles may be employed. Suitable covehicles include polyhydric aliphatic compounds such as ethylene, propylene or butylene glycols and their lower polymers, propylene glycol dipelargonate and other polyhydric alcohols such as glycerol. Thickening agents may be added to prevent settling and to improve the application characteristics and adherence of the composition on the skin surfaces. Suitable thickening agents include stearic acid, sodium stearate, cetyl alcohol, hydroxypropyl cellulose, Carbopol 940 (carboxyvinyl polymer, product of B. F. Goodrich Chemical Co.) and the like. If the liquid composition is to be a spray composition, anticlogging agents such as isopropyl, butyl, ethyl, and amyl palmitates, myristates, oleates, stearates and isostearates may be added. Other suitable agents are esters or water-soluble aliphatic alcohols having from 1 to 6 carbon atoms and fatty acids having from 10 to 24 carbon atoms. Still other suitable agents are silicones similar to those which may be used in aerosol spray compositions. Thus, the silicones enumerated as suitable in aerosol sprays except those specifically designated as volatile are contemplated in the liquid compositions. Other optional material such as fragrance, preservatives, dyes, etc. may also be added.

In the liquid compositions, the aldehyde polysaccharide compound active ingredient may be present in an amount from about 1 to about 20 percent by weight of the total composition. The thickening agent may be employed in an amount from about 0.05 to about 5 percent, depending on the nature of the agent. Thus, thickening agents such as hydroxypropylcellulose tend to be required in significantly smaller quantities than agents such as stearic acid. If the liquid composition is to be a spray composition, an anticlogging agent may be employed in an amount of from about 0.5 to 5 percent. A covehicle, if employed, may be added in an amount of from about 3 to 12 percent by weight. Fragrance and other optional ingredients may be added in amounts up to about 1 percent by weight.

The liquid compositions may be prepared by intimately mixing all the components except the aldehyde polysaccharide, fragrance and a portion of the ultimate liquid carrier or vehicle until a homogeneous mixture is obtained. To the resulting mixture is added the aldehyde polysaccharide compound and the mixing continued until a homogeneous dispersion is obtained. Thereafter, fragrance and other optional ingredients, if employed, is added, followed by the remainder of the liquid vehicle.

Liquid compositions may be modified for various methods of application and provided as lotions, roll on compositions, sprays and the like. For such uses appropriate covehicles, emollients and surfactants known to the skilled in the art may be added.

Another type of composition is one in which a wax solid is employed as a carrier. Such a composition is frequently supplied in the form of a "gel stick." In such compositions the aldehyde polysaccharide may be admixed with a liquid vehicle and distributed throughout a wax carrier with the aid of a surfactant agent. Such compositions may contain additional wetting agents. The preferred liquid vehicles are alcoholic in nature and include lower molecular weight alcohols as well as glycols. Generally, a blend of alcohol and a polyhydroxy compound are preferred. Suitable alcohols include ethanol, methanol, isopropanol, etc. Suitable polyhydroxy compounds include propylene glycol, ethylene glycol and glycols of relatively low molecular weights, and glycerol. Surfactants suitable for suspending the aldehyde polysaccharides include polyoxyethylated ethers of long chain alcohols and polyoxyethylated esters of long chain acids. Suitable agents include those previously enumerated such as polyoxyethylene monostearate, hexadecyl alcohol or isocetyl alcohol (Standamul G-16, Henkel, Inc.). In addition, lower alkyl esters of fatty acids are included to improve wetting properties at the epidermal surfaces. Suitable waxes include fatty amides such as monoethanolamide of stearic acid, diethanolamide of stearic acid, isopropanolamide of stearic acid and are available under trade names such as, for example, Emcol-7OH (Witco Chemical Corp., New York, N.Y.) and Monamide S (Mona Industries, Inc., Patterson, N.J.).

In compositions in waxy solid carriers, the aldehyde polysaccharide active ingredient may be employed in an amount of from about 5 to about 25 percent by weight of the total formulation. The wax may be employed in amounts of from about 15 to 50 percent by weight. The surfactant may be employed in amounts from about 0.1 to 5 percent by weight. The solvents are employed in from about 15 to 55 percent by weight with the ratio of alcohol to glycol ranging from about to 1:0.5 to 1:2.

The composition may be prepared by adding wax in small portions to glycol solvent heated to about 80° C. (75°–85° C.) and continuing the heating until the wax is melted, thereafter cooling to about 75° C. and adding the suspending surfactant and continuing the stirring until the surfactant is thoroughly mixed. When the mixture is about 65° C., the aldehyde polysaccharide is added and stirred vigorously for thorough mixing. Additional wetting agent, if employed, and alcoholic vehicle are then added with stirring. Fragrance and other optional ingredients may be added at this time. The mixture is then poured into molds and cooled rapidly to room temperature, preferably in a cold water bath. The waxy composition may then be employed for perspiration control.

By applying aldehyde polysaccharide compounds and compositions comprising aldehyde polysaccharide compounds to epidermal surfaces according to the present invention, effective inhibition of perspiration may be achieved which frequently exceeds the effectiveness of commercially available antiperspirants.

The effectiveness may be demonstrated in a test employing a rat foot pad as a model. The method, reported by A.B.G. Lansdown in J. Soc. Cosmet. Chem 24, 667–684 (1973), takes advantage of the fact that the laboratory rat has glands on the digital, metacarpal and metatarsal foot pads which morphologically resemble human eccrine sweat glands and that both the human and rat sweat glands respond similarly to injections of cholinergic drugs. It simulates the pharmacological excitation of human sweat glands using the rat foot pad model with cholinergic drugs such as methacholine, carbachol and pilocarpine to induce sweating. Thus, perspiration is induced by subcutaneous pilocarpine injection in the dorsal cervical region and the sweat production observed under a dissecting microscope, after staining the active pores with starch-iodine or o-phthalaldehyde to aid the visual observation.

A modification of the reported method has been adapted for the present determination of the efficacy of aldehyde polysaccharides. In the present determination, groups of male albino rats weighing between 180–200 grams are used for each composition. The rats are prepared for treatment and observation by lightly anesthetizing them and restraining their feet in a suitable device. Before treatment, both hind paws are cleaned to remove grease and adherent debris. The antiperspirant compositions then are applied to one hind paw while the other hind paw is left as an untreated control. The rats are suspended with their paws hanging free for four hours, after which time the rats are removed from the restraining device, again lightly anesthetized and prepared for observation of the plantar surfaces of the feet with a dissecting microscope. To aid in the visual observation, the starchiodine pore staining method is employed wherein both hind paws are first swabbed with a 2 percent iodine in ethanol solution, allowed to dry, and thereafter swabbed with a 50 percent suspension of starch in sesame oil. The treated paws then are injected with a 0.15 ml. amount of a 2 percent solution of pilocarpine hydrochloride, the injection being made into the dorsal subcutis in the cervical region to induce sweating. Observations are made of the treated and control paws for the time elapsed before appearance of sweat and/or the volume of sweat produced after a given time interval. The data obtained is then expressed as the mean sweating time (MST) and/or sweat volume score. The mean sweating time is defined as the time required after pilocarpine injection, for sweat to appear on all eleven foot pads: 5 digital, 4 interdigital and 2 metatarsal. The sweat volume score determination made in the present modification is obtained by grading the volume of sweat produced ten minutes following pilocarpine injection. Grading sweat volume score is done on a zero to 10 scale ranging from no sweating on any of the pads to profuse sweating on all of the eleven foot pads. By making similar observations on the treated foot, the value is given which reflects efficacy of antiperspirant. The average value for each group is given as the volume score for a particular antiperspirant. The extent of delay in the mean sweating time and/or the reduction in the perspiration output of the treated foot pad as compared with untreated controls indicates the antiperspirant efficacy of the test composition.

From the results of determinations employing the foregoing method, superior control of perspiration is seen as illustrated in representative operations in the working examples. In addition, the aldehyde polysaccharide compounds and compositions containing them are found not only to be effective in inhibiting perspiration but to be free of undesirable properties such as staining of the skin and common fabrics.

The property of absence of undesirable skin staining characterizing aldehyde polysaccharide compounds may be seen, for example, in representative determinations made of skin staining potential on albino guinea pigs employing dialdehyde cellulose compositions of different oxidation levels and employing unoxidized cellulose as controls. No gross staining of skin is observed in any instance. This property may be illustrated by the determinations carried out by employing a 10 percent (weight/weight) dispersion in 0.2 percent tragacanth solution of 80 percent oxidized dialdehyde cellulose and a similar dispersion of 66.4 percent oxidized dialdehyde cellulose. These compositions are applied topically twice a day to denuded skin (epilated 72 hours prior to use with wax) at a volume of 0.05 milliliter per application to an area of about 1 square inches for five consecutive days and the skin examined prior to each application and after the tenth application. In determinations and examinations for evidence of staining so made, no staining is evident. Similar determination employing a 10 percent (weight/weight) of an 88.7 percent oxidized dialdehyde starch in an autoclaved aqueous dispersion also showed no evidence of staining. It has been observed that compositions may tend to build up at the site of application rendering the skin whitish in color but on rinsing with water the whitish materials are readily removed leaving no evidence of staining.

In contrast to metallic salt antiperspirants which are known often to cause discoloration or permanent staining of fabrics on contact of metallic salts to the fabric, the aldehyde polysaccharides may be employed for the control of perspiration without causing permanent staining or discoloration of common fabrics. This property may be illustrated in representative determinations made of fabric staining potential employing a 5 percent dialdehyde cellulose aerosol of the following composition:

| Component | Percent By Weight |
|---|---|
| Dialdehyde cellulose (325 mesh, 80.7% oxidized) | 5 |
| Polydimethylsiloxane (Dow Corning Fluid F-218) | 5 |
| Polysorbate 20 | 0.1 |
| Fragrance | 0.15 |
| Propellant 12/Propellant 114 (40/60) | 89.75 |

The determinations are carried out by depositing the foregoing composition on various colored and white fabrics with and without simultaneous application of a composition simulating sweat and making observations in the following manner: The dialdehyde polysaccharide is sprayed onto the fabric surfaces from a distance of about 3 inches for 5 seconds until about 200 milligrams of composition has been deposited as determined by weighing the fabrics before and after application. Thereafter, a sweat simulating composition of the following composition is applied to some of the fabrics:

| Ingredient | Percent Weight/Volume |
|---|---|
| Acetic acid | 0.25 |
| Propionic acid | 0.25 |
| Butyric acid | 0.25 |
| Valeric acid | 0.10 |
| Crotonic acid | 0.10 |
| Acrylic acid | 0.10 |
| Inorganic concentrate* | 2.00 (v/v) |
| Distilled water | q.s. to 100.00 |

*Aqueous solution of the following in parts by weight to 100 parts by volume of solution: 0.5 NaCl, 0.04 KCl, 0.008 MgCl$_2$, 0.006 CaCl$_2$, 0.032 urea, 0.002 dextrose and 0.035 lactic acid.

After application, the test fabrics then are stored at ambient temperature for 48 hours and thereafter visually observed. Following this, the fabrics are rinsed with water, dried, and again examined for stains. It is found that when the foregoing operations are carried out on white fabrics of 100 percent cotton, 35 percent cotton plus 65 percent polyester, 100 percent polyester, 100 percent acetate, 100 percent rayon, and on colored fabrics of 100 percent acetate, 100 percent acrylic, 100 percent triacetate, and 100 percent nylon, stains are not developed and no alteration of color shades or patterns are noticed on the colored fabrics.

The following examples illustrate the invention but are not to be construed as limiting.

EXAMPLE I

The effectiveness of dialdehyde cellulose as antiperspirant is determined and compared with unoxidized cellulose in a test for efficiency in inhibiting pilocarpine-induced sweating according to the modified Lansdown procedure employing the following compositions.

The dialdehyde cellulose and cellulose compositions are prepared as follows:

| Dialdehyde Cellulose (DAC) Composition I | |
|---|---|
| Component | Weight |
| Dialdehyde cellulose (79.4 percent oxidized) | 1.0 gram |
| Tragacanth (0.2 percent solution) | 9.0 gram |

| Cellulose Composition | |
|---|---|
| Component | Weight |
| Microcrystalline cellulose | 1.5 gram |
| Tragacanth (0.2 percent solution) | 13.5 gram |

The compositions are prepared by mixing the dialdehyde cellulose or cellulose (which previously has been milled and passed through a 325 mesh screen to insure uniform particle size (less than 44 μm)) with a 0.2 percent tragacanth solution to obtain a homogeneous suspension.

The 0.2 percent tragacanth solution employed is prepared by mixing together 1.0 gram of tragacanth gum, 0.15 gram of methyl paraben* and 498.85 gram of distilled water thereafter passing through a hand homogenizer.

*In the preparation of microcrystalline cellulose composition N-(3-chloroalkyl)hexaminum chloride is employed instead of methyl paraben as preservative.

The compositions are employed in the modified Lansdown procedure previously described employing groups of ten male rats weighing 180–200 grams for each composition. The test is carried out by applying the test solutions to the left hind paw of each animal while restrained, the paw previously having been cleaned with distilled water and dried. The application is made with a cotton stick applicator saturated with the respective compositions. After four hours, the rats are removed from the restraining device, anesthetized and their paws prepared for observation. Thereafter they are injected with pilocarpine hydrochloride and observations made in the manner previously described for time elapsed before the appearance of sweat and for the volume of sweat 10 minutes after injection.

The results expressed as means sweating time and sweat volume score are as follows:

| Composition | Mean Sweating Time* '(Min) "(Sec.) | | | Sweat Volume* Score | | |
|---|---|---|---|---|---|---|
| | Control | Treated | Difference | Control | Treated | Difference |
| DAC | 4'0" | 8'30" | 4'30" | 10 | 3 | 7 |
| Cellulose | 3'20" | 4'20" | 1'0" | 7 | 8 | −1** |

*Results statistically significant at 95 percent confidence level.
**Increase in Sweat Volume Score.

EXAMPLE II

A 10 percent dialdehyde starch composition is prepared as described below and the efficacy as antiperspirant determined in rat foot pad test in a similar manner.

The dialdehyde starch composition is prepared by mixing 60 grams of dialdehyde starch (95 percent oxidized) with 532.8 grams of distilled water, autoclaving the mixture at 120° C. for 20 minutes, and thereafter adding with stirring a solution of 0.15 gram of methyl paraben and 0.05 gram of propyl paraben in 1.0 gram of ethanol (200 proof), followed by centrifuging the resulting suspension at 10,000 r.p.m. for 30 minutes and filtering to obtain the treating composition.

In the test operation, groups of five male rats are employed. The dialdehyde starch composition is applied to the right hind foot of each animal which previously has been cleaned with a 50:50 mixture of ether-ethanol to remove grease and debris. Applications are made twice a day for four days and on the fifth day, between two to three hours after the first application, the mean sweating time is measured in the manner previously described. The results show that the mean sweating time for dialdehyde starch treated paw is 2.4 minutes as compared to 2.1 minutes for control. The results of observation made on volume of perspiration produced show that although there is some evidence of perspiration immediately as seen in the mean sweating time, the volume does not increase significantly during the 10 minute observation period while in the control paws there are large volumes of sweat at the end of the 10 minute period.

EXAMPLE III

Dialdehyde polysaccharide compositions are prepared as follows:

Dialdehyde Cellulose Composition II (DAC II)

A 15 percent (weight/volume) homogeneous dispersion of dialdehyde cellulose is prepared by intimately admixing 15 grams of dialdehyde cellulose (80% oxidized), 8.5 grams of a 0.2 percent (weight/weight) aqueous dispersion of tragacanth and sufficient water to make up to 100%.

Dialdehyde Starch Composition II (DAS-II)

A 10 percent (weight/weight) colloidal dispersion of dialdehyde starch is prepared by first autoclaving 10.0 grams of dialdehyde starch (89% oxidized) and 88.8 grams of distilled water at 120° C. for twenty minutes; then, after first replacing the water lost on autoclaving, adding to the autoclaved dispression a solution of 0.15 gram of methyl paraben and 0.05 gram of propyl paraben in 1.0 gram of ethanol; thereafter centrifuging the resulting dispersion at 10,000 r.p.m. for thirty minutes; and then filtering to remove a minor amount of residue and to obtain a homogeneous dispersion.

The above compositions are employed to determine efficacy as an antiperspirant manifested by inhibition of pilocarpine induced sweating in a modified Lansdown procedure in a manner similar to that described in Example I and measuring mean sweating time and sweat volume and comparing with controls. The results (based on the average of 10 rats) are as follows:

| Composition | Mean Sweating Time (Minutes) | | | Sweat Volume Score | | |
|---|---|---|---|---|---|---|
| | Control | Treated | Difference | Control | Treated | Difference |
| DAC-II | 2.36 | 9.1 | 6.74* | 10.0 | 0.4 | 9.6* |
| DAS-II | 1.55 | 6.31 | 4.76* | 10.0 | 1.2 | 8.8* |

*Significantly different at a 95 percent level of probability.

EXAMPLE IV

Compositions are prepared from dialdehyde cellulose in a manner similar to that described in Examples I and III, but in which the dialdehyde cellulose is employed at different concentrations. The compositions are employed in the modified Lansdown procedure as described in Example I. The results expressed as sweat volumne score and difference in sweat volume score (average of 10 rats) are seen in the table below. The table also gives the percent weight of the aldehyde group in the composition.

| Dialdehyde Cellulose Concentration Percent (Weight/Weight) | Degree of Oxidation (Percent) | Weight of Aldehyde Group (Percent) | Sweat Volume (Score)* | | |
|---|---|---|---|---|---|
| | | | Control | Treated | Difference |
| 7.49 | 79.37 | 2.0 | 10.0 | 8.3 | 1.7 |
| 3.61 | 79.37 | 1.0 | 10.0 | 7.5 | 2.5 |
| 2.87 | 79.37 | 0.8 | 9.2 | 6.3 | 1.9 |
| 1.77 | 79.37 | 0.5 | 10.0 | 8.0 | 2.0 |
| 1.05 | 79.37 | 0.3 | 10.0 | 7.8 | 2.2 |
| 0.70 | 79.37 | 0.2 | 10.0 | 7.9 | 2.1 |

*Significant at a 95 percent confidence level.

EXAMPLE V

Compositions are prepared from dialdehyde cellulose in a manner similar to that described in Examples I and III in which the level of oxidation of the dialdehyde cellulose is varied. The compositions are employed in the procedure described in Example I and the mean sweating time and sweat volume score determined. The results (average of 10 rats) expressed as delay in means sweating time and decrease in sweat volume are seen in the following table. The table also gives the percent weight of the aldehyde group in the composition.

| Dialdehyde Cellulose Concentration (Weight/Weight) | Degree of Oxidation | Weight of Aldehyde Group | Decrease in Sweat Volume Score* | Delay in MST (Secs.) |
|---|---|---|---|---|
| 10% | 79.37% | 2.9% | 7.0 | 270* |
| 10% | 55.47% | 2.4% | 2.0 | 156* |
| 10% | 32.32% | 1.2% | 2.0 | 170* |
| 10% | 8.96% | 0.4% | 2.0 | 90 |

*Significant at a 95 percent confidence level.

EXAMPLE VI

A 15 percent DAC Suspension Composition is prepared for rat foot pad testing by mixing together 16.4 grams of dialdehyde cellulose (200 mesh, 82.7 percent oxidixed) with 83.60 grams of a 0.2 percent gum tragacanth-sorbic acid homogenized dispersion. The latter is prepared by mixing together 0.2 grams of gum tragacanth, 0.2 gram of sorbic acid and 83.2 gram of distilled water.

The foregoing DAC Suspension Composition and two commercial antiperspirants, Antiperspirant A and B are employed in the manner previously described for in vivo antiperspiracy evaluation in the rat foot pad test. The results obtained are as follows:

| Composition | Mean Sweating Time (Seconds) | | | Sweat Volume Score | | |
|---|---|---|---|---|---|---|
| | Control | Treated | Difference | Control | Treated | Difference |
| DAC (15%) Suspension Composition | 53.5 | 410.0 | 356.6* | 10.0 | 2.2 | 7.8* |
| Commercial Antiperspirant A | 43.1 | 98.0 | 54.9* | 10.0 | 5.1 | 4.9* |
| Commercial Antiperspirant B | 60.0 | 95.5 | 35.5 | 10.0 | 7.7 | 2.3* |

*Significant at a 95 percent confidence level.

EXAMPLE VII

Liquid dialdehyde cellulose (DAC) compositions of varying dialdehyde cellulose concentrations, cosmetically suitable for application to the skin and having the following compositions are prepared:

| DAC Liquid Composition A | |
|---|---|
| Component | Percent Weight/Weight |
| Dialdehyde cellulose (82.7 percent oxidized) | 15.0 |
| Stearic acid | 2.0 |
| Propylene glycol | 2.0 |
| Fumed silica | 5.0 |
| Arlacel 186 (Glyceryl monoleate with propylene glycol, ICI America, Inc., Altas Chemicals Div.) | 0.5 |
| Ethanol (200 proof) | 75.5 |

| DAC Liquid Composition B | |
|---|---|
| Component | Percent Weight/Weight |
| Dialdehyde cellulose (82.7 percent oxidized) | 15.0 |
| Stearic acid | 4.0 |
| Propylene glycol | 5.0 |
| Hydroxypropyl cellulose | 0.5 |
| Arlacel 186 | 1.0 |
| Ethanol (200 proof) | 74.5 |

| DAC Liquid Composition C | |
|---|---|
| Component | Percent Weight/Weight |
| Dialdehyde cellulose (82.7 percent oxidized) | 15.0 |
| Stearic acid | 2.0 |
| Propylene glycol | 2.0 |
| Bentone Gel IPM (10% bentone, 86.7% isopropyl myristate, 3.3% wetting agent, NL Industries) | 3.0 |
| Arlacel 186 | 1.0 |
| Ethanol (200 proof) | 77.0 |

The foregoing compositions are prepared by adding to ethanol, sequentially and with stirring after addition of each component or group of components to obtain a homogeneous solution: stearic acid, propylene glycol and the appropriate thickening agent, and then glyceryl monoleate with propylene glycol. To this mixture is added dialdehyde cellulose portion wise and with stirring to obtain a uniform dispersion. Thereafter, the mixture is weighed and ethanol as needed is added.

The compositions are useful in delaying time before sweating and in decreasing the volume of sweat produced.

EXAMPLE VIII

A powder antiperspirant composition suitable for dusting is prepared having the following components:

| Powder Composition | |
|---|---|
| Component | Percent By Weight |
| Dialdehyde cellulose (82.7% oxidized) | 15 |
| Tricalcium phosphate | 2 |
| Magnesium stearate | 0.5 |
| Calcium stearate | 0.5 |
| Talc | 1 |
| Corn starch | 80.35 |
| Fragrance | 0.65 |

The composition is prepared by first separately sieving tricalcium phosphate, magnesium stearate, calcium stearate and corn starch through a 200 mesh sieve, then weighing out the appropriate amounts and mixing thoroughly. Thereafter, 200 mesh sieved dialdehyde cellulose is added and the resulting composition mixed again. The fragrance is then added and mixed to produce a powder composition of the above formulation.

The composition is suitable for dusting onto skin surfaces to inhibit perspiration.

EXAMPLE IX

A liquid composition suitable for use as a pump spray composition is prepared having the following components:

| Liquid Spray Composition | |
|---|---|
| Component | Percent By Weight |
| Dialdehyde cellulose (82.7 percent oxidized) | 5 |
| Isopropyl myristate | 1 |
| Stearic acid | 3 |
| Hydroxypropyl cellulose | 0.4 |
| Fragrance | 0.2 |
| Ethanol | 90.4 |

The composition is prepared by thoroughly mixing the appropriate amounts of isopropyl myristate, stearic acid and hydroxypropyl cellulose with a portion of the ethanol. To the mixture is added dialdehyde cellulose with stirring until it is thoroughly dispersed. Fragrance is then added and the remainder of ethanol then added and mixed.

The resulting composition is suitable for spraying onto the skin surfaces from a liquid pump spray dispenser for the control of perspiration.

EXAMPLE X

A gel stick composition comprising dialdehyde cellulose in a waxy solid as carrier is prepared having the following composition:

Gel Stick Composition

| Component | Percent By Weight |
| --- | --- |
| Dialdehyde cellulose (82.7 percent oxidized) | 20 |
| Propylene glycol | 22 |
| Emcol 70H (stearamide,monoethanolamine wax) | 26 |
| Isocetyl alcohol | 11.3 |
| Isopropyl palmitate | 2 |
| Ethanol (200 proof) | 18.2 |
| Fragrance | 0.5 |

The gel stick is prepared by adding the stearamide monoethanolamine wax portionwise to the propylene glycol heated to 80° C. until the wax is melted. The mixture is cooled to 75° C. and the isocetyl alcohol added and stirring continued until the temperature reaches 65° C. The dialdehyde cellulose is then added slowly and the resulting mixture stirred vigorously. Thereafter, isopropyl palmitate and ethanol are added while the temperature is still about 65° C. Frangrance is then added and the mixture stirred thoroughly and then poured into appropriate containers and cooled rapidly to room temperature by shaking the containers slowly in a cold water bath.

The resulting gel stick is suitable for application to the skin surfaces for inhibition of perspiration.

EXAMPLE XI

A liquid antiperspirant composition having the following components is prepared in a manner similar to that described in Example VII.

Liquid Composition

| Component | Percent By Weight |
| --- | --- |
| Dialdehyde starch (85% oxidized) | 15 |
| Stearic acid | 2 |
| Propylene glycol | 2 |
| Fumed silica | 5 |
| Arlacel 186 | 0.5 |
| Fragrance | 0.2 |
| Ethanol (200 proof) | 75.3 |

The composition is suitable for application to the skin surfaces for inhibition of perspiration.

EXAMPLE XII

In a manner similar to that described in Example VIII, the following composition is prepared

| Component | Percent By Weight |
| --- | --- |
| Dialdehyde starch (95 percent oxidized) | 15 |
| Tricalcium phosphate | 2 |
| Magnesium stearate | 0.5 |
| Calcium stearate | 0.5 |
| Talc | 1 |
| Corn starch | 80.35 |
| Fragrance | 0.65 |

The composition is suitable for application to the skin surfaces for inhibition of perspiration.

EXAMPLE XIII

Aerosol spray compositions are prepared having the following components:

Aerosol Composition A

| Component | Percent By Weight |
| --- | --- |
| Dialdehyde Cellulose (80% oxidized) | 8 |
| Isopropyl myristate | 5 |
| Fragrance | 0.2 |
| Propellants 12/114 (40/60) | 86.8 |

Aerosol Composition B

| Component | Percent By Weight |
| --- | --- |
| Dialdehyde Starch (90% oxidized) | 5 |
| Polydimethylsiloxane | 5 |
| Fragrance | 0.2 |
| Propellants 12/114 (40/60) | 89.8 |

The aerosol compositions are prepared by placing the appropriate aldehyde polysaccharide previously screened through a 325 mesh sieve in the container. Thereafter, a mixture of fragrance and lubricant previously filtered through a fiber filter is charged into the container. Thereafter, the container is filled with the propellant mixture.

The compositions are useful for applying to the skin surfaces to inhibit perspiration.

EXAMPLE XIV

In a manner similar to that described in Example X, the following gel stick composition is prepared:

| Component | Percent By Weight |
| --- | --- |
| Dialdehyde starch (90 percent oxidized) | 20 |
| Propylene glycol | 22 |
| Emcol 70H | 26 |
| Isocetyl alcohol | 11.3 |
| Isopropyl palmitate | 2 |
| Ethanol (200 proof) | 18.2 |
| Fragrance | 0.5 |

The composition is suitable for application to the skin surfaces for inhibition of perspiration.

EXAMPLE XV

In a manner similar to that described in Example XIII, the following aerosol composition is prepared:

| Component | Percent By Weight |
| --- | --- |
| Dialdehyde cellulose (80% oxidized) | 5 |
| Polydimethylsiloxane | 5 |
| Fragrance | 0.15 |
| Propellants 12/114 (40/60) | q.s. to 100 |

The composition is suitable for application to the skin surfaces for inhibition of perspiration.

EXAMPLE XVI

In a manner similar to that described in Example IX, the following liquid spray composition is prepared:

| Component | Percent By Weight |
| --- | --- |
| Dialdehyde cellulose (75 percent oxidized) | 10 |
| Isopropyl myristate | 1 |
| Stearic acid | 3 |

| Component | Percent By Weight |
|---|---|
| Ethanol (200 proof) | 86 |

The composition is suitable for application to the skin surfaces for inhibition of perspiration.

EXAMPLE XVII

In a manner similar to that described in Example VIII, the following composition is prepared.

| Component | Percent By Weight |
|---|---|
| Dialdehyde starch (95 percent oxidized) | .35 |
| Tricalcium phosphate | 1.5 |
| Magnesium stearate | 0.5 |
| Calcium stearate | 0.5 |
| Talc | 2 |
| Corn starch | 59.85 |
| Fragrance | 0.65 |

The composition is suitable for application to the skin surfaces for inhibition of perspiration.

EXAMPLE XVIII

In a manner similar to that described in Example X, the following gel stick composition is prepared:

| Component | Percent By Weight |
|---|---|
| Dialdehyde starch (90 percent oxidized) | 2 |
| Propylene glycol | 30 |
| Emcol 70H | 34 |
| Isocetyl alcohol | 11.8 |
| Isopropyl palmitate | 2.5 |
| Ethanol (200 proof) | 19.2 |
| Fragrance | 0.5 |

The composition is suitable for application to the skin surfaces for inhibition of perspiration.

EXAMPLE XIX

In separate operations, dialdyhyde celluloses each having a degree of oxidation of about 75 percent are prepared by periodate oxidation from cellulosed having the following appropriate degrees of polymerization: (a) about 500 repeating units, (b) about 1000 repeating units and (c) about 1500 repeating units. The resulting dialdehyde celluloses are employed to prepare compositions similar to that described in Example VIII. The compositions are suitable for applying to skin surfaces to inhibit perspiration.

What is claimed is:

1. A method for reducing the volume of perspiration produced which comprises applying to the epidermal surface area where reduction in volume of perspiration is desired, a perspiration volume reducing amount of a substantially water-insoluble aldehyde polysaccharide compound.

2. A method according to claim 1 in which the aldehyde polysaccharide compound is at least 10 percent oxidized.

3. A method according to claim 1 in which the aldehyde polysaccharide compound is one which has been prepared from a polysaccharide having a degree of polymerization of at least 400 repeating units per molecule.

4. A method according to claim 1 wherein the aldehyde polysaccharide compound is applied in an amount sufficient to supply 0.02 mg. to 1 mg. per square cm. of epidermal surface.

5. A method according to claim 1 in which the aldehyde polysaccharide compound is a dialdehyde starch.

6. A method according to claim 1 in which the aldehyde polysaccharide compound is a dialdehyde cellulose.

7. A method according to claim 1 in which the aldehyde polysaccharide compound is supplied in a composition containing said aldehyde polysaccharide compound in an amount of at least 0.5 percent by weight of ultimate composition.

8. A method according to claim 1 in which the aldehyde polysaccharide compound is present in the composition in an amount sufficient to supply at least 0.2 percent by weight of the aldehyde group.

* * * * *

UNITED STATES PATENT AND TRADEMARK OFFICE
CERTIFICATE OF CORRECTION

PATENT NO. : 4,263,274
DATED : April 21, 1981
INVENTOR(S) : Ann B. Kulkarni and Kakublai R. Vora It is certified that error appears in the above-identified patent and that said Letters Patent are hereby corrected as shown below:

On the title page, Item /75/ add -- Charles H. Beede --.

Signed and Sealed this

Twentieth Day of October 1981

[SEAL]

Attest:

GERALD J. MOSSINGHOFF

Attesting Officer     Commissioner of Patents and Trademarks